United States Patent [19]

Inouci

[11] Patent Number: 4,846,145
[45] Date of Patent: Jul. 11, 1989

[54] INFRARED RAY RADIATION SAUNA DEVICE WITH HEAT SOURCE OF COMBUSTION HEAT

[76] Inventor: Katsuyoshi Inouci, 1-2-601, Namiki 2-chome, Kanazawa-ku, Yokohama-shi, Kanagawa 236, Japan

[21] Appl. No.: 59,544
[22] PCT Filed: Oct. 9, 1986
[86] PCT No.: PCT/JP86/00518
 § 371 Date: Jun. 8, 1987
 § 102(e) Date: Jun. 8, 1987
[87] PCT Pub. No.: WO87/02238
 PCT Pub. Date: Apr. 23, 1987

[30] Foreign Application Priority Data

Oct. 11, 1985 [JP] Japan ................................ 60-155452
Dec. 11, 1985 [JP] Japan ................................ 60-190624
May 30, 1986 [JP] Japan ................................ 61-124899

[51] Int. Cl.$^4$ ................................................ A61F 7/00
[52] U.S. Cl. ......................................... 126/208; 126/84; 126/91 A; 126/116 B; 4/524
[58] Field of Search .............. 126/204, 208, 84, 91 A, 126/91 R, 116 B; 4/524 X; 237/69, 70 X, 76

[56] References Cited

U.S. PATENT DOCUMENTS

| 2,682,867 | 7/1954 | Cartter | 126/116 B |
| 3,828,762 | 8/1974 | Duzey | 126/91 A |
| 4,044,751 | 8/1977 | Johnson | 126/91 A |
| 4,277,855 | 7/1981 | Pass | 4/524 |

FOREIGN PATENT DOCUMENTS

| 2123739 | 12/1972 | Fed. Rep. of Germany | 4/524 |
| 98926 | 12/1981 | Japan . | |
| 131341 | 2/1982 | Japan . | |
| 169450 | 3/1982 | Japan . | |
| 21297 | 7/1982 | Japan . | |
| 59-162174 | 10/1984 | Japan . | |
| 60-131970 | 8/1985 | Japan . | |

*Primary Examiner*—Randall L. Green
*Attorney, Agent, or Firm*—William D. Hall

[57] ABSTRACT

This invention relates to a sauna device with an infrared ray radiation sauna heater such that cooling air is introduced into the infrared ray radiation tube heated by combustion heat of fuel such as gas or the like to lower the temperature of the infrared ray radiation tube and radiate far infrared ray absorbable into the human body.

It can be made up as the compact sauna device usable in home equipping the combustion devices in a box like mechanic chamber (114) placed at lower portion of the seat (111) in the sauna chamber.

It is able to assemble, as the rear wall (102), the side walls (105, 107) the front wall (108) and the ceiling plate (104) can be assembled by engaging the project and groove joint.

Attaching laundry rod holders (2210-1, 2210-2) containing a safety switch in the sauna chamber, on which the laundry rod (2209) is hung, it is available to use the sauna chamber as a drying chamber for laundry.

7 Claims, 10 Drawing Sheets

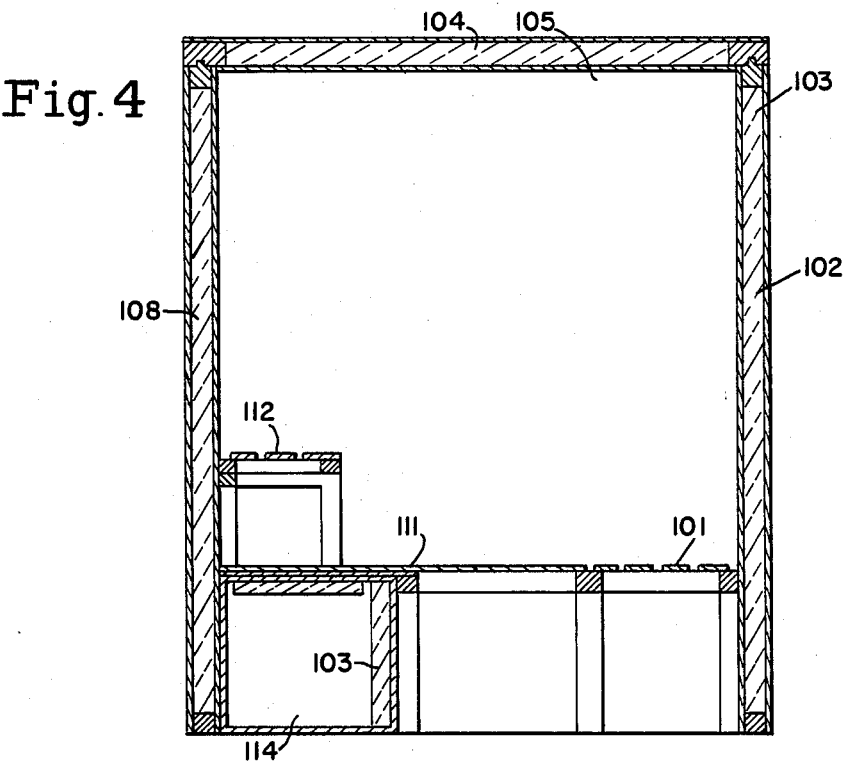
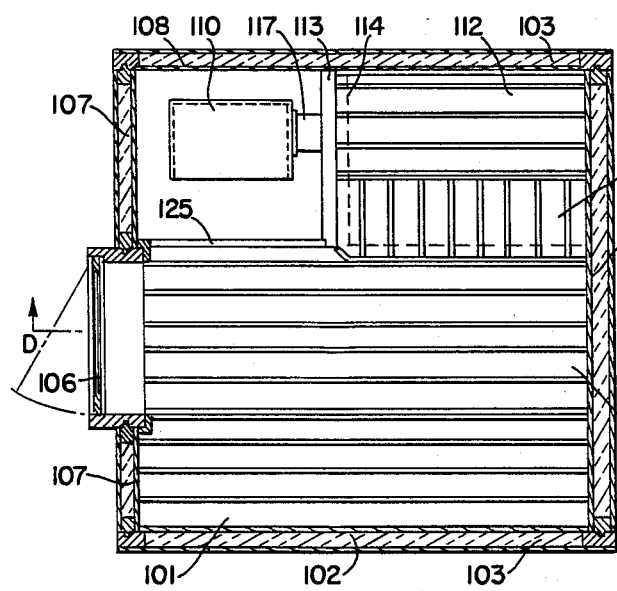
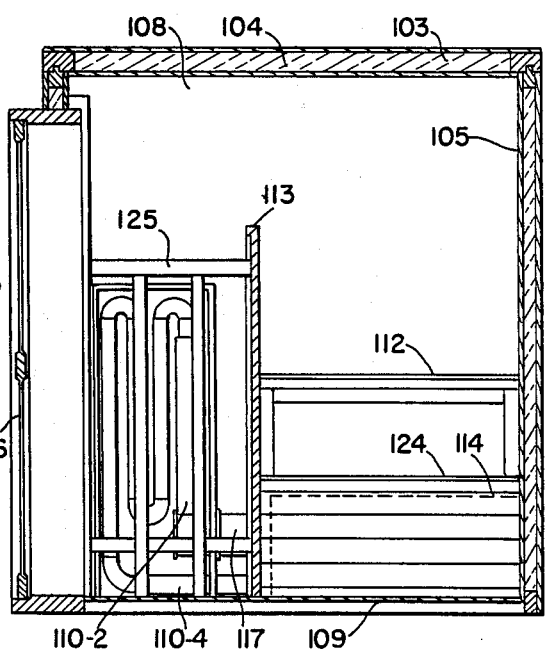

INFRARED RAY RADIATION SAUNA DEVICE WITH HEAT SOURCE OF COMBUSTION HEAT

TECHNICAL ART FIELD

This invention relates to a sauna device having an infrared radiation sauna heater, more particularly an improvement of the sauna device having an infrared ray radiation sauna heater for the heat source. Combustion of fuel is converted to an infrared heat for the sauna.

BACKGROUND ART

The conventional sauna device of the convection type employing an electric heater is popular, but it has a disadvantage that electric energy is expensive.

To overcome such disadvantage, convenient and economical sauna devices were developed, wherein liquid or gas fuel is burned. The heat of combustion was converted to infrared rays which radiate the heat to the human body.

The infrared ray radiation device usually employs the burner and other combustion device outside the sauna chamber since it is dangerous to burn fuel in the sauna chamber. The combustion heater devices require broader floor space than sauna device with electrical heat source.

These problems are more serious for smaller scale sauna.

Although sauna devices to overcome the above disadvantages are disclosed in the specifications of Japanese utility model application Nos. 59-162174 and 60-131970, the devices there disclosed require a larger relatively floor space in comparison with an electric type sauna device with conventional electrical heat source.

The conventional infrared ray radiation sauna device does not provide the desired heat efficiency, safety and easeness of maintenance or inspection work.

DISCLOSURE OF INVENTION

This invention relates to a device which solves the above problems and one of the objects of the invention is to provide (a) infrared ray radiation sauna device suitable for use in the home (b) a sauna requiring the least possible floor space.

A second object of the invention is to provide an infrared ray radiation sauna device with high safety.

A third object of the invention is to provide an infrared ray radiation sauna device which is easily maintainable and inspectable.

A fourth object of the invention is to provide an infrared ray radiation sauna device which is low in cost and a compact in construction.

A fifth object of invention is to provide an infrared ray radiation sauna device with (a) low fuel cost (-- using petroleum and gas, etc. and (b) requiring flow space.

An object of the invention is achieved by an infrared ray radiation sauna device having a combustion heat source which comprises an infrared ray radiating tube, etc., wherein an infrared ray radiator is provided in the sauna chamber, in the tube of which gas or liquid fuel is burned or combustion gas is blown in the tube and infrared ray is radiated from the outer surface of the tube; and seats are located facing the infrared ray radiator with a partition between them, in a direction that the infrared ray of the infrared ray radiator is radiated; a control box at least partly covered with heat insulating is mounted in said seats, to insulate at the boundary between the control box and the inside wall of the sauna chamber; and a blast pipe passes inside of the control box to the combustion chamber of the infrared ray radiator, under the floor, to supply fuel and combustion air to the combustion chamber; and an exhaust tube or pipe which communicates from the downstream of the radiator pipe of the infrared ray radiator passing, under the floor, to inside of the control box and the inside of the control box contains the devices such as an electromagnetic valve which are necessary for fuel supply, and appliances such as a blower for exhausting, a transformer for ignition which is necessary for normal combustion devices; and upper and side walls of the control box is constructed detachably, so that the combustion heat is the heat source.

BRIEF DESCRIPTION OF THE ACCOMPANYING DRAWINGS

FIG. 4 is a cross section along line C—C in FIG. 1;

FIG. 5 is a horizontal cross sectional plan view showing additional embodiment of the infrared ray radiation sauna device of the invention;

FIG. 6 is a cross section along line D—D in FIG. 5;

BEST MODE OF THE INVENTION

Figure 1:
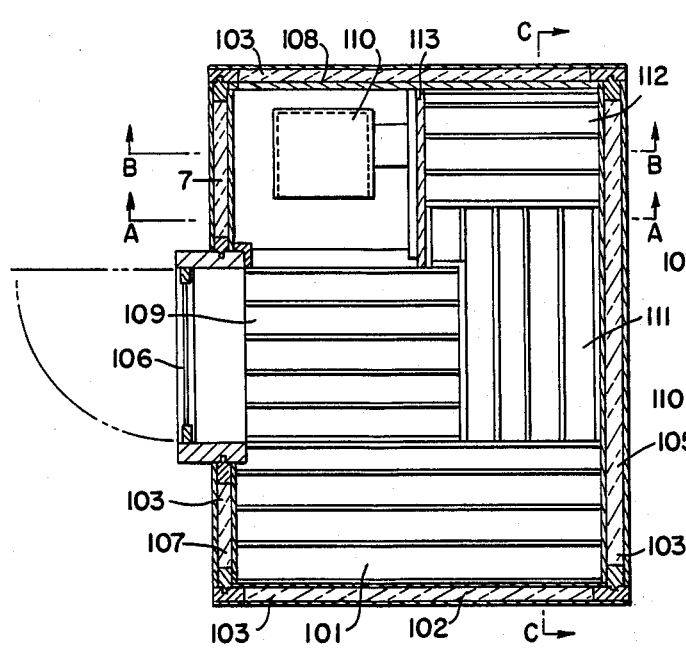
FIG. 1 is a horizontal cross sectional plan view of an embodiment of the infrared ray radiation sauna device of the invention.
Figure 2:
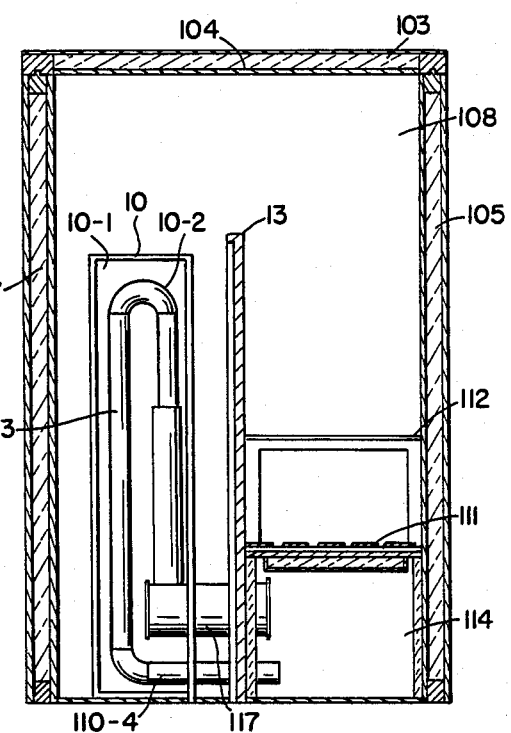
FIG. 2 is a cross section taken along line A—A in FIG. 1.
Figure 3:
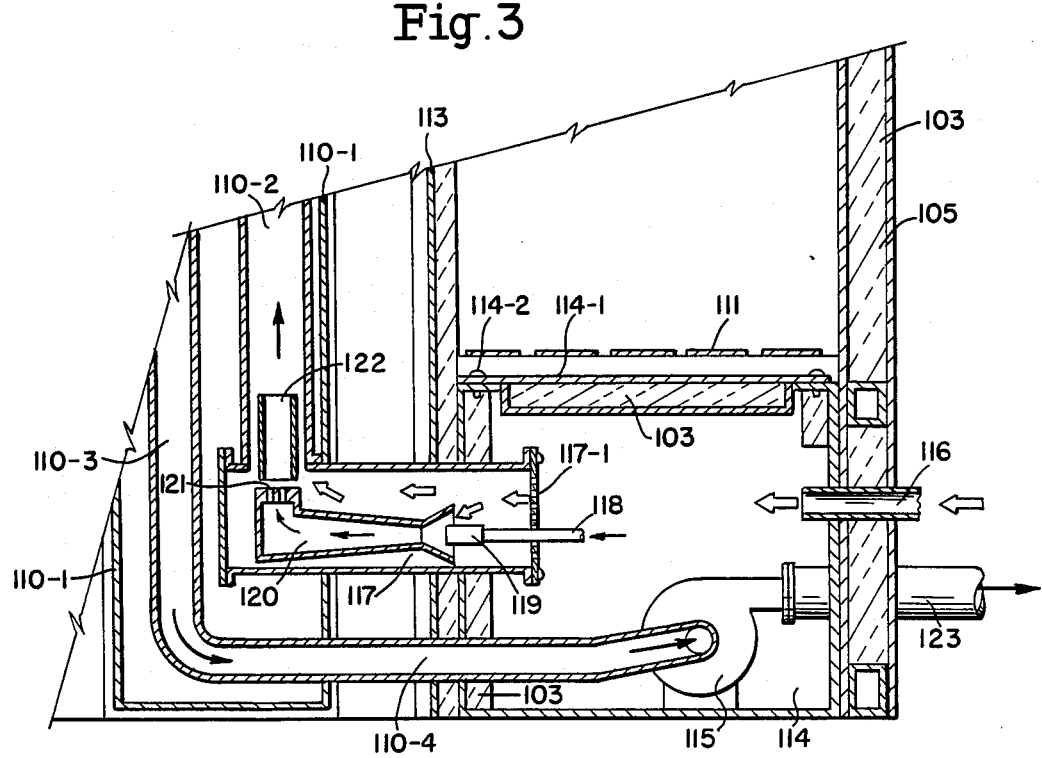
FIG. 3 is a cross section along line B—B in FIG. 1.

The first embodiment of the infrared ray radiation sauna device of this invention is hereinafter explained with reference to the accompanying FIG. 1 through FIG. 4.

The rear wall 102 is provided with a space which is stuffed with heat insulating material such as glass wool, etc. The upper end of the rear wall 102 is interlinked to the ceiling plate 104 with a tongue and groove joint, and the right side and left side edges of wall 102 are interlinked by the right side wall 105 and to the left side wall 107. Wall 107 is provided with an inlet. The ceiling plate 104, right side wall 105 and left side wall 107 are stuffed with heat insulating member 103 to provided insulation as in the rear wall 102.

A front wall 108 opposed to the seat 101 and rear wall 102 is engaged with the ceiling plate 104, the right side wall 105 and the left side wall 107 in the above mentioned manner, and is insulated in the same manner. Between the seat 101 and the front wall 108, as shown in FIG. 1, a floor board 109 is close to the seats 101, and an infrared ray radiation member 110 is mounted near the front wall 108.

The infrared ray radiating member 110 is surrounded by a reflecting plate 10-1 which has good radiation characteristics such as aluminum, at its left and right side faces, upper and lower faces and rear face (--, excluding the front face which is opposed to the seats 101 --). A combustion heat radiating tube 10-2 and a radiator tube 110-3, communicating to the combustion heat radiating tube 10-2 at its upper portion, are provided upwardly and downwardly in a vertical direction respectively, and inside the the reflecting plate 110-1.

A side seat 111 is provided on the sauna chamber side of the right side wall 105 opposed to a door 106 which is on left side of the seats 101.

The side seat 111 has the same height as the seat 101. Seat 111 has one end which connects a front end of the seat 101 and its another end extends to the front wall 108. The upper wall (seating plate) of seat 111 is detachably constituted.

Adjacent the front wall 108 111 is an upper seat 112 which is easily detached. A protection plate 113 is provided between the upper seat 112 and tube 10 of the infrared ray radiator 110, so that person who sits down on the upper seat 112 will not be injured by the infrared ray radiator 110'.

A metal control box 114 is provided in a space between protection plate 113 on lift side seeing from the seat 101 with right protection plate 113 and right side. The box 114 extends to seat 111 on upper side reaching to the footing board 109 on front beneath side seats 111 and 112 and reaches to the floor board 109.

The metal control box 114 is insulated by heat insulating materials 103 at the inside space of the wall facing the sauna chamber, and a cover 114-1 insulated by the heat insulating material 103 is detachably mounted by a bolt 114-2, at the top portion.

Contained in the metal control box 114 are components, such as an ignition transformer for an electromagnetic valve, gas pipe arrangement (not shown) and a blower 115 for exhaustion.

Air for combustion is introduced into the blast tube 117 from the inlet 117-1 of the blast tube 117, through the in-take tube 116 by suction power of the exhaust blower 115, as shown by the white thick arrow mark.

On the other hand, fuel gas passes as shown in black thin arrow mark, through an electromagnetic valve (not shown) etc., and a gas supply tube 118, and is injected into a mixer tube 120 from a nozzle 119, and at that time primary air for combustion is absorbed into the mixer tube 120. The mixer tube 120 is provided in the blast tube 117 which passes through the side wall of the metal box 114 and the protection plate 113 and arrives at inside of the infrared ray radiator 110, and the mixed gas which passes the mixture tube 120 comes into the internal combustion tube 122 from a fire nozzle 121 of the gas burner and contacts secondary air to support combustion.

The combustion flame causes the infrared rays from the outer surface of the combustion heat radiator tube 110-2 to heat the inside of the sauna chamber.

Combustion gas generated by combustion rises in the tube as shown by a black thick arrow mark and flows into the radiator tube 110-3 from upper part of the tube 110-2 and radiates the infrared rays from the outer surface of the tube in the same manner.

The combustion gas further comes down in the radiator tube 110-3 and flows into a radiator tube 110-4 which is positioned in a horizontal manner at lower part of the infrared ray radiator 110 and passes through the radiator 110-4 (which passes through the reflection plate 110-1 and the protection plate 113), into the metal box 114 and exhausted through the exhausting pipe 123 by the blower 115 for gas exhaustion.

The infrared ray radiation sauna device explained above is the first embodiment of this invention. When making the sauna device for three person according to this embodiment, outer dimensions of the sauna device are 160 cm in width, 120 cm in depth (length of the front portion of rear wall), 190 cm in height in round number.

If the dimensions are as above, one person can easily sit down on the seat 101, one person on side seat 111 and one person on upper seat 112.

FIGS. 5 and 6 show the second embodiment of the infrared ray radiating sauna device of this invention. FIG. 5 is the horizontal cross section al view and FIG. 6 is the cross section al view along line D—D in FIG. 5. The second embodiment device is slightly larger than the device of the first embodiment and about five persons can use it at the same time, and its outer dimensions are 170 cm in width, 170 cm in depth and 190 cm in height.

The construction of the second embodiment is same as the first embodiment, the basic points of difference are two respects that the additional installation of the infrared ray radiator is realized as the sauna chamber is bigger, and no side seat is provided.

Instead of the side seat 111, a low temperature seat 124 is provided at upper portion of the metal box shown by dotted line, opposed to the seat 101, the low temperature seat 124 is constructed as a lower step for the upper seat 112, so that it and is usable as a staircase to the upper seat 112.

125 is a protection fence so that a person on the footing board cannot fall down against the infrared ray radiator 110 side.

Three persons can sit on the seat 101 facing toward the infrared radiator 110, and two persons on the upper seat 112. Alternatively, three persons can sit on seat and one person at the upper seat 112 and one at the low temperature seat 124. Totally five persons can sit comfortably.

Thus, the advantages of the first and second embodiments of this invention are as follows: (1) An infrared ray radiation sauna device can be constructed in a small size so that a home, or a small scale facility, can benefit from the device. In other words, a mechanic chamber (metal box 114) is provided under the seats of the sauna chamber, inside of which a burner and other combustion device are installed, the infrared ray radiation sauna device with heat source of the combustion heat of the fuel can be constructed smaller by a large margin, its installation area is small and its height is also lower than the device with the mechanic chamber installed at the lower portion of the infrared ray radiation member. (2) The metal box 114 containing the components can be wider as required without increasing the floor space for the sauna device. In other words, in the first embodiment, the whole space under the side seat 111, if requested, can be used as the metal box 114, and furthermore the metal box 114 can be formed in L-shape, and also all the lower portion of the seat 110 can be a container space for the components. In the case of the large scale sauna device, wherein the attached instruments of large size are required, the entire inner space of the upper stage seat 112 can be used as the metal box so that a device with 70 cm height can be contained. (3) Mounting, detaching and maintenance of the components such as the burner in the metal box 114, are easily carried out. When the repair of the such device is requested, the upper seat 112 and side seat 11 are detached, and bolt 114-2 is removed and the cover 114-1 is detached for the repair. In that case, there is no need of the work by turning over on the seat, and the worker can work by standing on the footing board 109 which is lower than the seat or by attaching his knee on the footing board 109. (4) Manufacturing cost is reduced. In other words, as the entire device is compact, i.e. for a sauna for three persons, the entire outer surface is reduced by about 20% as compared to the conventional sauna, and its manufacturing cost may be reduced by 10%. As all the edges of the ceiling wall 104 and other walls, 102, 105, 107, 108 are engaged in tongue and groove joints, the device can be easily assembled and all the costs such as the transportation fee and labor cost etc., are reduced. (5) Fuel cost is reduced. In other words, heat loss from the sauna chamber results from flow out and in of the air and heat radiation from the outer surface of the sauna chamber, but the outer surface area is reduced by about 20% as mentioned above, the radiation area is reduced by 20%, hence the heat radiation loss is reduced by 20%.

As mentioned above, the infrared ray radiation sauna device of this invention has a lot of advantages. In view of the recent interest in sports and health, the sauna device which provides a pleasant sensation and health, with a heat source of the low price fuel, can be provided at a lower price. Moreover it is quite advantageous as it can be installed in the same space as in the electric power type sauna.

Although in the above embodiments, the device using gas as the fuel was shown, kerosene oil or the like is usable, if the gas burner inside the radiator tube 110-2 or the blast tube 117 is replaced by a conventional gaseous oil burner shown in JP U.M. 57-52710.

Thus, in the embodiments mentioned above, in the sauna device for five persons, having space to provide seats not only in the infrared ray radiating direction of the infrared ray radiation member, but also in non radiating direction side, the inside space of the seat provided in non radiating direction is used as a chamber for the components, however, in the sauna device of the infrared ray radiation type, it is desirable to radiate the infrared ray directly to human body. Therefore, in a smaller sauna for one to two persons, it is most desirable that a seat is provided in the direction of infrared ray radiation of the infrared ray radiator, so that a seated person on the seat is able to receive sufficiently radiation of the infrared ray.

FIGS. 7 through 12 show a further embodiment of my sauna device, wherein an infrared ray radiation sauna device operates from combustion heat, a seat is provided in the path of infrared ray radiation which is is most preferable direction, inside space of which includes a control box for components of the heater, the pipings for fuel and air supply communicate with the control box and the infrared ray radiation member and pass under the floor of the sauna chamber so that the infrared ray radiation sauna heater (having the heat source of combustion heat) becomes useful.

Figure 7:
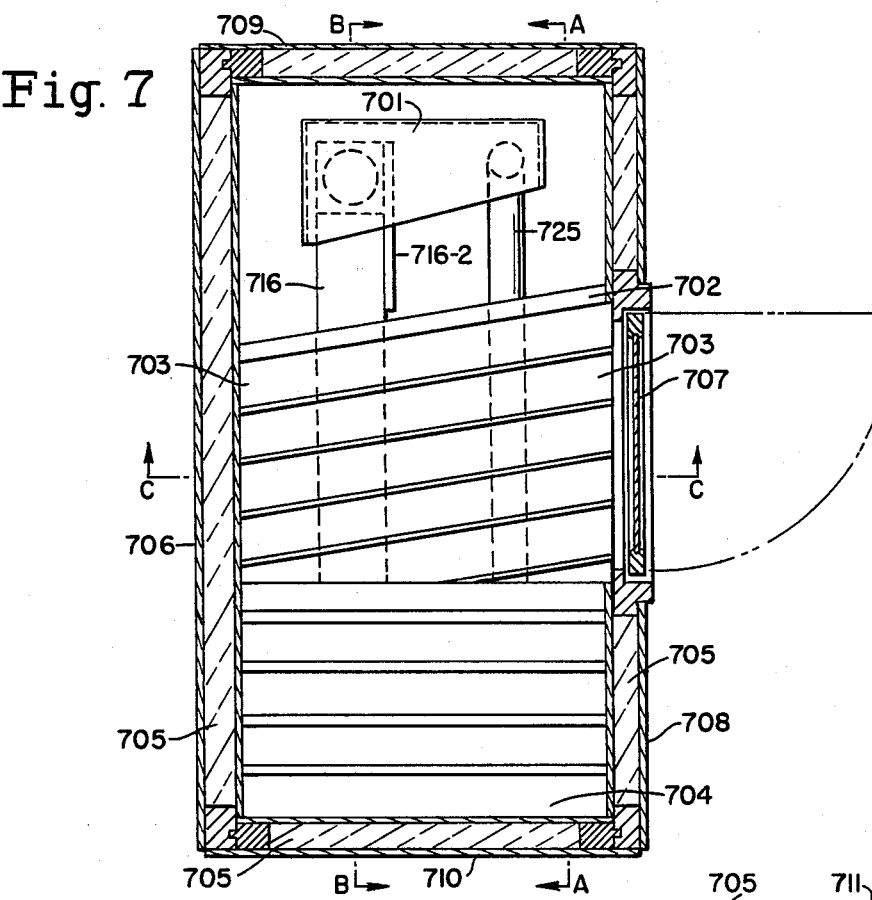
FIG. 7 is a further horizontal cross sectional plan view of the further embodiment of the infrared ray radiation sauna device of the invention.
Figure 8:
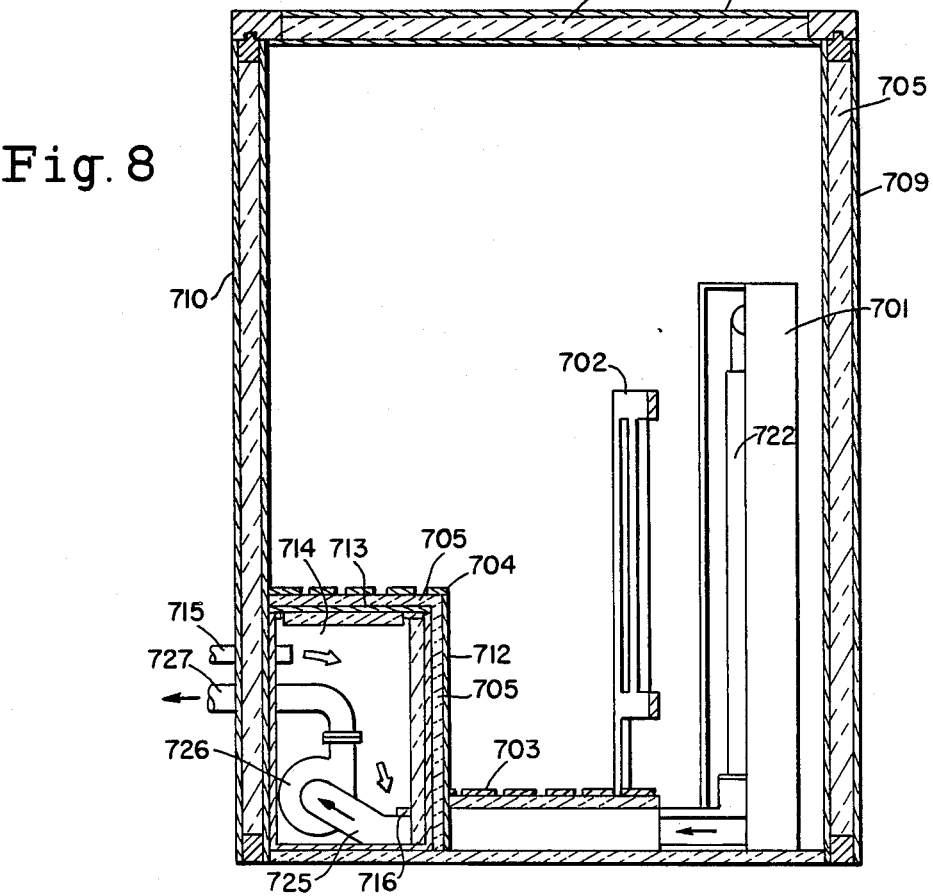
FIG. 8 is a cross section along line A—A in FIG. 7.
Figure 9:
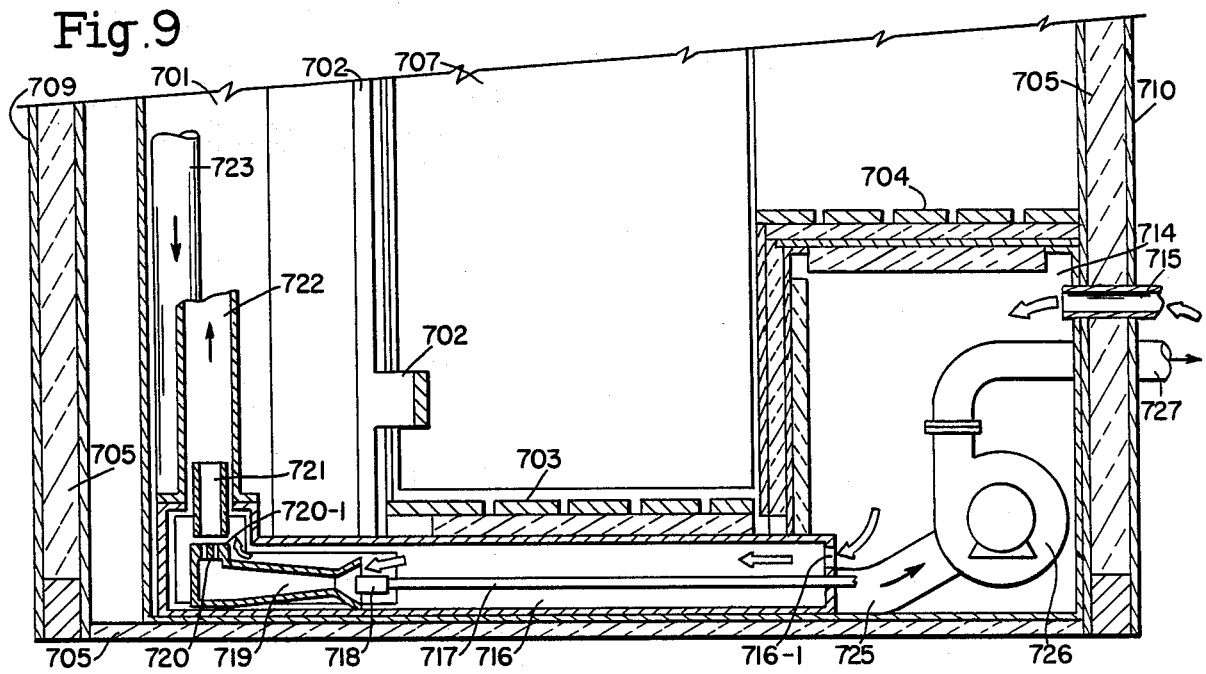
FIG. 9 is an enlarged cross section of lower part at cross section along line B—B in FIG. 7.
Figure 10:
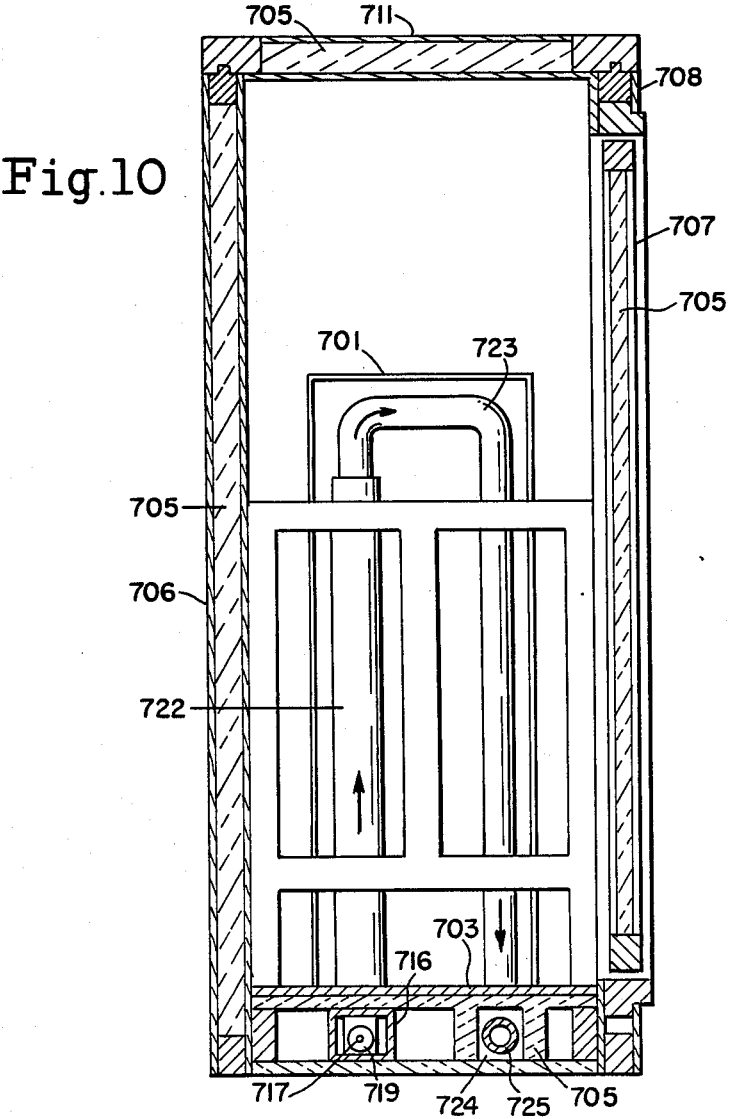
FIG. 10 is a cross section along line C—C in FIG. 7.

FIG. 7 is a horizontal cross sectional plan view of one embodiment of infrared ray radiation sauna device of above construction, FIG. 8 is a cross section taken along line A—A in FIG. 7, FIG. 9 is an enlarged cross section of lower part of cross section along line B—B in FIG. 7, and FIG. 10 is a cross section along line C—C in FIG. 7.

Seat 704 is provided at a position opposed to the infrared ray radiator. The protection fence 702 protects the person(s) using the sauna. The foot board 703 is on the floor. Left side wall 70b is provided on the left side of the seat 704, and a right side wall 708 having a door 707 on the right side, a the rear wall 709 at rear of the infrared ray radiator 701, and a rear wall 710 at the rear of the seat 704; and the inside of each wall is insulated by heat insulation material 705. The walls are connected together by tongue and groove joints as shown in FIG. 7, and a ceiling 711 is also engaged in the same manner and assembled to form a sauna chamber.

A wooden plate 712 is normally mounted on the sauna chamber side of the seat 704 and the inside surface of the plate 712 is covered with a heat insulating material 705, and also, a cover plate 713 is detachably mounted at the top side; and a heat insulated metal box control box 714 is installed in the seat 704. Into the. control box from outside, air for combustion flows through the air supply tube 715 as shown by white arrow marks, and the air flows into an blast tube 716 from a small hole 716-1 of the blast tube 716. A part of the combustion air entering into the blast tube 716 passes through an electromagnetic valve (not shown) provided in the control box 714, to mix with fuel gas jet out from a nozzle 718 through a gas pipe, and enters into a gas burner 720 through a mixing tube 719, and flows out into the combustion chamber 721 from an opening 720-1 to begin combustion.

Combustion gas rises up through an inside of a combustion heat radiation tube 722, in a direction shown by a black arrow mark and, converting the combustion heat to an infrared ray to heat the sauna chamber, and goes down through a radiator tube 723, and passes through an exhaust tube 727 in a path 724 which is defined and isolated by a heat insulating materials member 705 under the footing board 703 on the floor, and is suctioned into a blower 726 for exhaustion, and is forcedly exhaust to the outdoors through an external exhaustion tube 727.

When repair and inspection of the gas burner 720 is requested, and inspection plate 716-2 (See FIG. 7) is removed, which closes the burner inspection hole provided on a side wall of the blast tube 716, and the gas burner 720 is drawn out in the direction of the radiator tube 723, and repaired.

When repair and inspection of the components located in the control box 714, such as the blower 726 for exhaustion, is required, the seat 704 is removed so that upwardly, then the cover 713 is removed a worker's hand can be inserted into the control box 714 to easily conduct repair.

The necessary height for the blast tube 716 under the footing board 703 is the height to accommodate the mixture pipe 719, as there is no need of pulling it out to the control box side when the burner is removed; it is about 6-7 cm for the sauna device for one to two persons, and its height from the floor surface to the footing board 703 even including the heat insulating materials member is about 14-15 cm therefore there is no need of the very high sauna chamber in comparison with the conventional type.

As the exhaust tube 712 is smaller than the blast pipe 716, there is no problem in the case.

Thus, as the embodiment shown in FIGS. 7 to 10 is a sauna chamber for one person, its outer dimensions are 130 cm in width, 75 cm in depth (width of the rear wall 709 or sear rear wall 710) and 190 cm in height.

Figure 11:
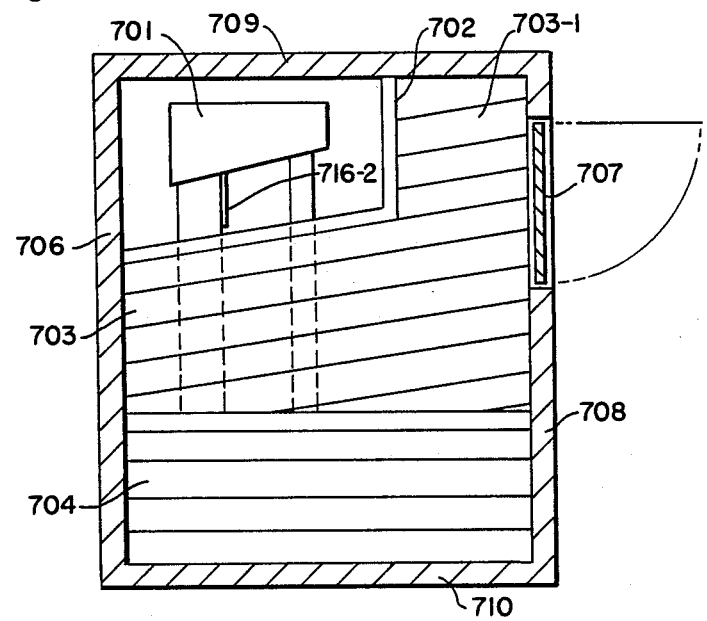
FIG. 11 is a horizontal cross sectional plan view showing further embodiment of the infrared ray radiating sauna device of the invention.

Next, FIG. 11 is a horizontal sectional view showing a further embodiment of the infrared ray radiation sauna device, and in this embodiment, the depth of 75 cm shown in the embodiment in FIG. 7 is lengthened by about 50 cm, so that two persons can use the sauna at the same time. This construction is almost the same as the embodiment in FIG. 7, but the door 707 is moved toward the rear wall 709, to make easy going in and out of the door 707, when there is a person at the extension (right side) of the seat 704, as there is a surplus area on the floor for an extended foot board 703-1 adjacent to infrared ray radiation member 701.

Hence, the outer dimensions for the embodiment in FIG. 11 are about 130 cm in width, 125 cm in depth, and 190 cm in height.

Figure 12:
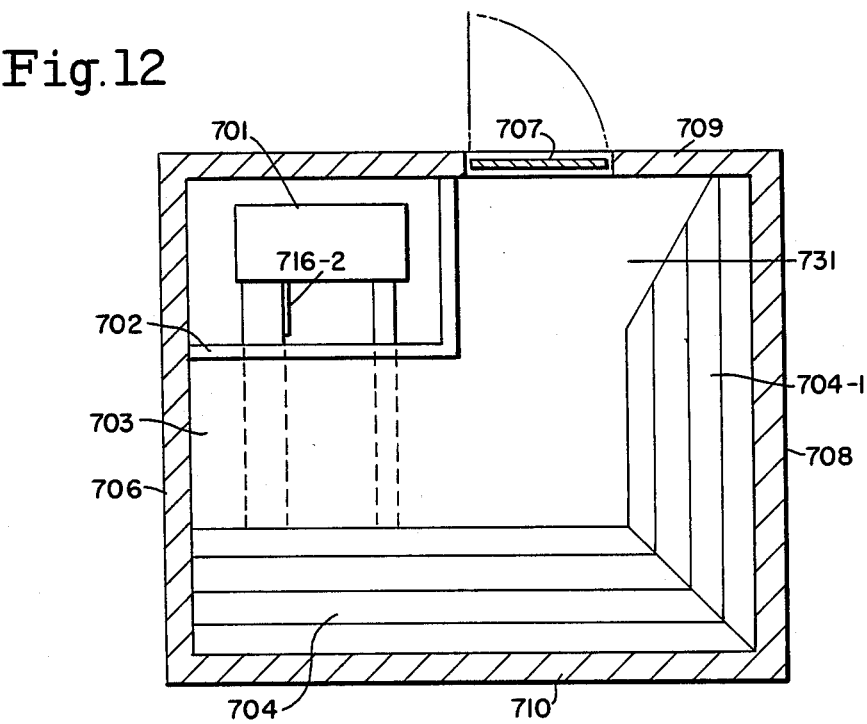
FIG. 12 is a horizontal cross sectional plan view showing further embodiment.

FIG. 12 shows a horizontal sectional view of a further different embodiment of this invention, whereby this is for the sauna chamber for 3-4 persons at the same time bathing and the door 707 is provided on the side of the rear wall 709, and an additional seat 704-1 is provided on the side of the sauna chamber of the right side wall 708, and the infrared ray radiator 701 is of a larger size as required for the larger sized sauna chamber.

Two persons can sit comfortably on the seat 704, and one comfortably on the additional seat 704-1, or two persons can sit down on the both seats, respectively but a little tightly. Outer dimensions in this embodiment are about 170 cm in width, 140 cm in depth and 190 cm in height.

Thus, the light beam of long wave length (called the far infrared ray) is easily absorbed into a human body, or various organic objects, and particularly a beam of a wavelength of 4-10 micro meters, preferably about 6 micrometers, is known as suitable for room heating or for a sauna.

Wave length of the light beam is determined by temperature of an object emitting the light, and the beam of about 6 micrometers wave length is emitted by a radiator which is at 210° C., according to Wein's Displacement Law.

Thus, in a case of the far infrared ray radiator, with a heat source of electric power, it is easy to maintain the heater temperature at about 210° C. In the far infrared ray radiator with the heat source of fuel combustion heat, however, it is hard to maintain a surface temperature of the radiation surface at the specified constant value.

Because the temperature of the burning flame is normally at about 1500°-200° C., an outer surface temperature in the combustion chamber becomes 800°-1500° C. unless water cooling or forcible air cooling is used. In this case, the temperature becomes considerably higher than said 210° C. (the temperature that I have said was suitable for far infrared ray radiation). Hence, the wave length of about 6 micrometers would not be realized, and also breakage of the combustion chamber may occur.

On the other hand, it is preferable that the temperature of the radiating body near the exhaust portion is as low as practicable, generally at about 150° C., as heat efficiency is better with lower temperature of the exhaust gas.

Therefore, there is a need to lower the temperature at the outer surface of the high temperature part of the combustion chamber or the like, if a high heat efficiency is required.

A method was found to lower the outer surface temperature of the combustion chamber by providing concentric cylinders the inner one of which is the combustion chamber, and cooling air is forcibly supplied between the inner and outer cylinders to cool the outer surface of the inner cylinder and the inner surface of the outer cylinder. The outlet of the inner cylinder extends beyond the point where combustion is completely finished. Hence the cooling air is mixed with a high temperature combustion gas flowing from the inside of the inner cylindrical member so as to lower the temperature of the combustion gas. This keeps the outer combustion cylinder at a suitable lower temperature.

Upon applying the method, the temperature of the radiator at its downstream end might be lower than is the case with no cooling air.

As an example when, the radiator is actually used as the heat source for room heating, sauna, drying, etc. two or three times the theoretical amount of air necessary for perfect combustion is forcibly applied between the inner and the outer cylinders, to keep the temperature of the outer cylinder surface at its hottest portion to 450°-550° C. (which produces radiation of a wavelength of 4-7 micrometers which is in the far infrared portion of the spectrum.

While such infrared ray radiation has an advantage in that the wave length is suitable for sauna and is absorbable into human body, excess air is heated and exhausted together with exhaustion gas, with the consequent disadvantage that the heat efficiency is lowered.

At present, in this kind of far infrared ray radiator generally two mode change over control of combustion and stop (two postion control) for temperature control is popular, but more recently, three position control of high combustion, low combustion and stop or combustion control such as proportional control, etc., in some part are introduced for and its demand is increasing. However, if the cooling air flow system between the inner and outer cylinder as mentioned above is applied to such three position controlled far infrared ray radiation device, a sharp fall of the heat efficiency occurs.

In other words, in the conventional far infrared ray radiation device, the flow rate of combustion air is also automatically increased and decreased when the flow rate of fuel is increased and decreased and as the flow rate of cooling air is automatically increased and decreased in direct ratio to the combustion air, a sharp Fall of the heat efficiency.

To solve this problem, it is advisable to apply a control method of the the rate combustion and air for the later discussed far infrared ray radiation device, in the infrared ray radiation sauna device according to this invention.

Namely, in the control method, when the combustion is decreased, the cooling air is reduced as required so as to keep the temperature of the combustion outer cylinder at the desired radiating temperature.

In other words, temperature of the outer combustion cylinder falls if the flow rate of cooling air is decreased in direct ratio to the flow rate of combustion air, when the combustion is decreased; the flow rate of cooling air is greatly decreased under that of the conventional devices so that the temperature of the combustion cylinder becomes at the same degree as the time of high combustion, to automatically decrease the exhaustion gas at the low combustion to improve the heat efficiency.

This control method will be discussed with reference to FIGS. 13 through 15.

Figure 13:
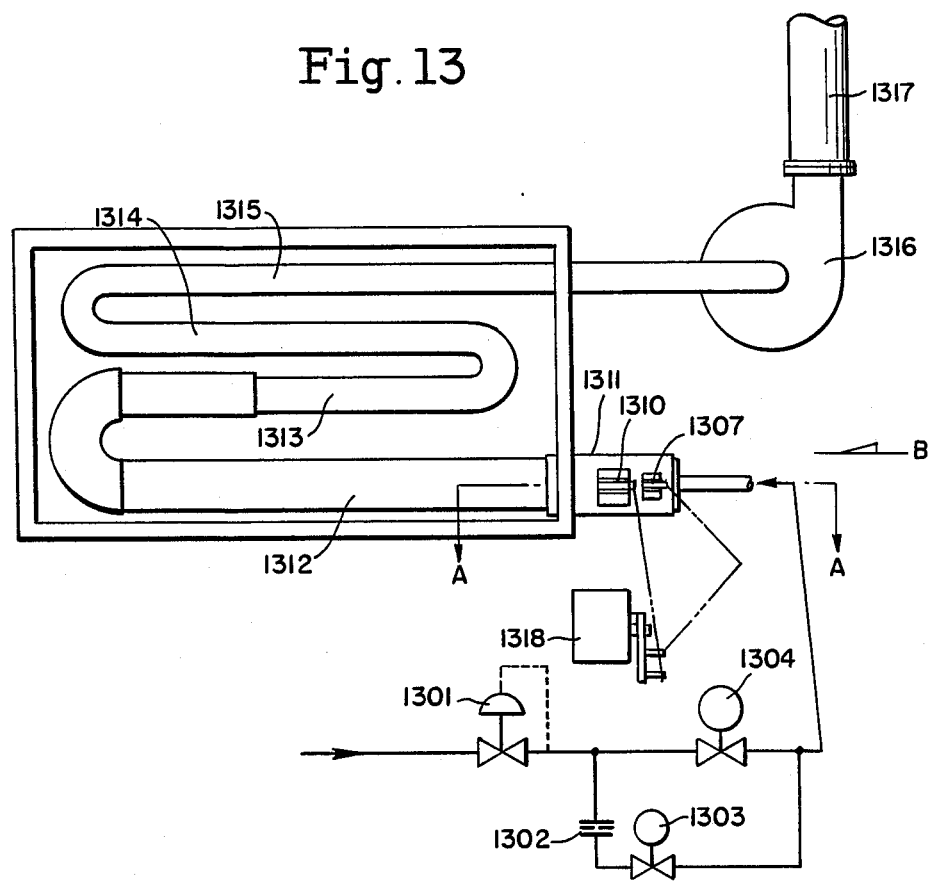
FIG. 13 is a front view showing one embodiment of the combustion device to conduct novel control method of the combustion and air in the sauna heater of the infrared ray radiation sauna device of the invention.

FIG. 13 is a front view showing one embodiment of the combustion device to conduct the above mentioned novel control method of the combustion rate and flow rate of air. FIG. 14 is a cross section along line A—A in FIG. 13, and FIG. 15 is a partial enlarged scale view seen from an arrow mark in FIG. 13.

The fuel gas almost flows to a high combustion electromagnetic valve 1304 after passing a governor 1301, and a relatively small amount of gas passes through an orifice 1302, and passes through a low combustion electromagnetic valve 1303 and joins with large gas passed the high combustion electromagnetic valve 1304 and flows into a gas burner 1306 located in the combustion inner cylinder.

Figure 14:
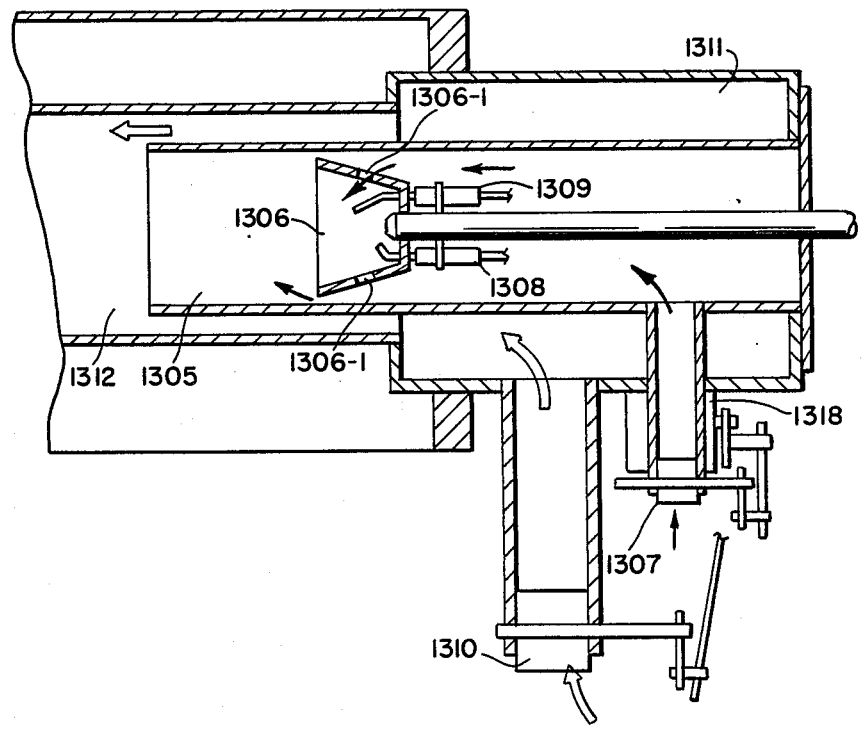
FIG. 14 is an enlarged cross section along line A—A in FIG. 13.

On the other hand, the air for combustion enters in the combustion inner cylinder after passing the combustion air damper 1307 and flows into the gas burner 1306 from a small hole 1306-1 of the gas burner 1306 as shown by a fat black arrow marks in FIG. 14 and mixes with the fuel gas.

Numerals 1308 and 1309 form an ignition spark gap and an electrode bar for flame detection.

Furthermore, the cooling air enters into a duct 1311 from a cooling air damper 1310, and passes between the combustion outer cylinders 1312 and inner cylinder 1305 to cool both cylinders and gradually mix with the combustion gas downstream of the outlet of the combustion inner cylinder 1305, and passes the far infrared ray radiators 1313, 1314, 1315 and passes through exhaust blower 1316 and is exhausted from a chimney to outside.

The above stage is a state at high combustion, but there are instances where the combustion speed has to be decreased, according to the state of the heated article.

In this case, when a signal is given for changing over to low combustion, the electromagnetic valve 1304 automatically closes to shut off the main supply line of the fuel gas, and gas is allowed to flow only through the line of the low combustion electromagnetic valve 1303.

Hence, in this instance, the flow rate of gas is decreased by the resistance of an orifice 1302. Namely, the gas flow is decreased to half of the flow rate at high combustion, in this embodiment.

At the same time, the combustion air damper 1307 and the cooling air damper 1310 (which are fully open under conditions of high combustion) are automatically closed to a certain degree by operation of a control motor 1318 so as to squeeze air supply.

Figure 15:
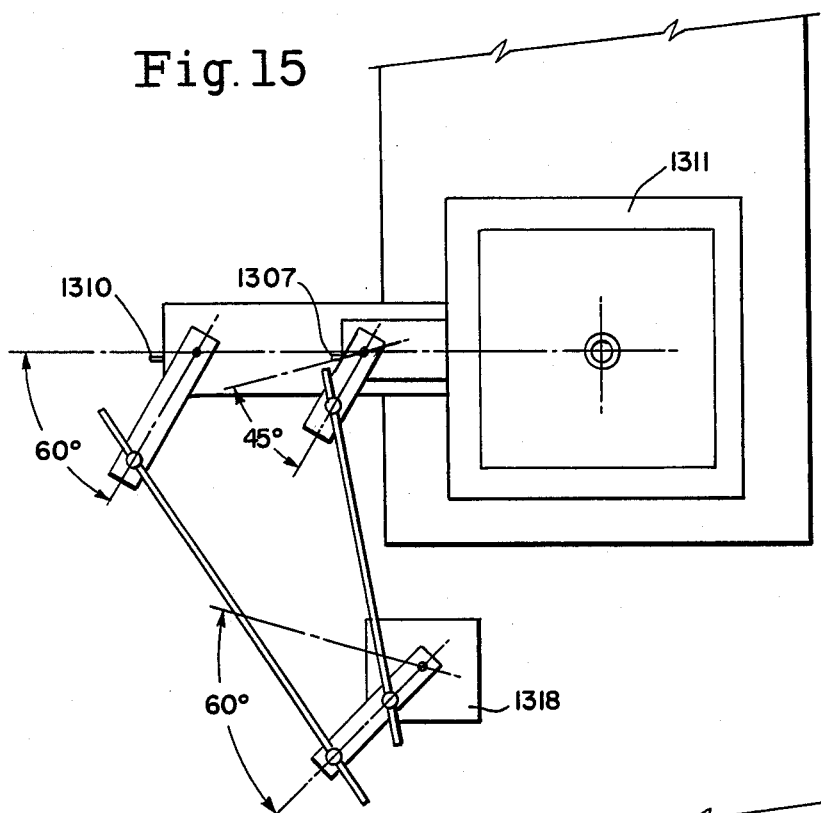
FIG. 15 is a partial enlarged view seen from arrow mark B direction in FIG. 13.

At this time as shown in FIG. 15, the combustion air damper 1307 closes for 45°, but the cooling air damper 1310 closes for 60°.

When the combustion damper 1307 closes for 45°, opening area becomes 30% of a full open (high combustion), but as the differential pressure across the damper increases, the flow rate of combustion air increases, and the combustion air decreases to about 60% of the high combustion in the above embodiment.

On the other hand, when the opening area of the cooling air damper 1310 decreases to 13% of the full open, the flow rate of cooling air becomes 30% of the flow rate during high combustion.

The flow rate of the exhaust gas, during low combustion is automatically decreased by the cooling air at low combustion. This controls the temperature of the outer combustion cylinder to keep it at the same temperature as it was at the high combustion time. Thus the heat efficiency of the far infrared ray radiation device used for the sauna device in this invention is greatly improved.

Figure 16:
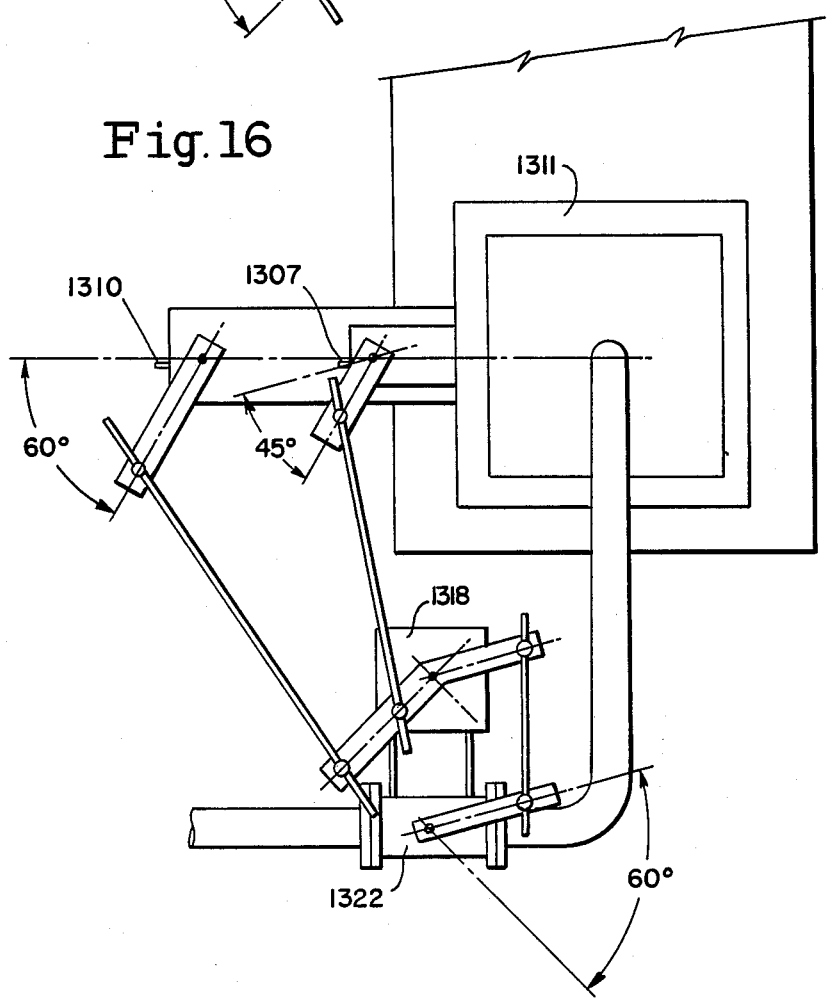
FIG. 16 is a partial enlarged view of one embodiment of the combustion device of proportional control system.

FIG. 16 shows the second embodiment of the combustion device to practice the above control method.

The combustion control in the embodiment shown in FIGS. 13 to 15 is the three position control of high combustion, low combustion and stop, but the device in the FIG. 16 is an embodiment of more high grade proportional control system.

The flow rate of combustion gas is proportional controlled by a butterfly valve 1322 interlinked with the control motor 1318, and when the control motor 1318 and the butterfly valve operate for maximum 60°, the combustion air damper 1307 is moved for a maximum of 45°, the cooling air damper 1310 for a maximum of 60°. Hence, the decrease in the rate of flow of the cooling air is always greater than that of the combustion air.

Figure 17:
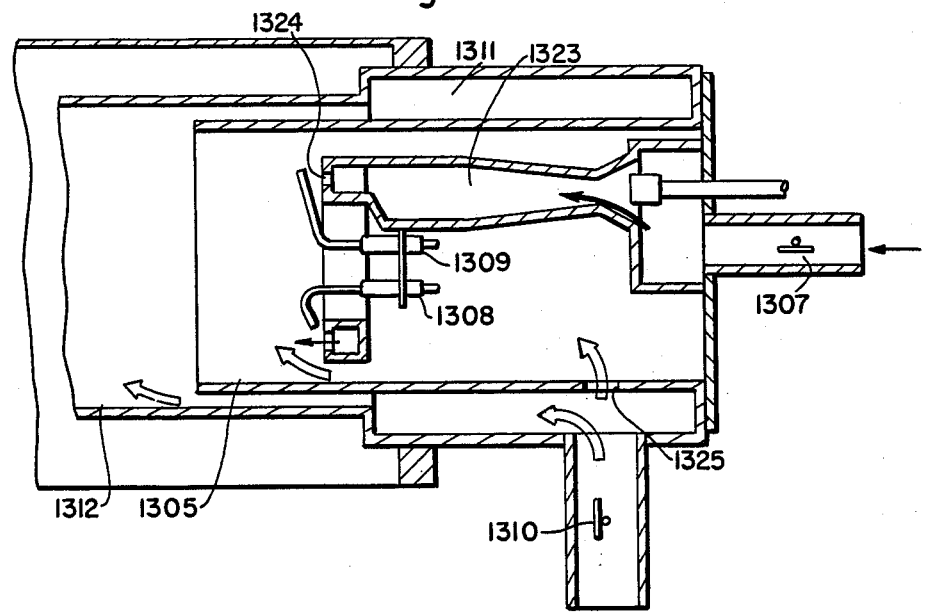
FIG. 17 is an enlarged view of one further embodiment of the burner part of the combustion device wherein there is a premixing type of gas burner.

FIG. 17 is an enlarged view showing the third embodiment of the burner part of the combustion device to carry out the above control method. Although the gas burner in the embodiments in FIGS. 13–15 is a nozzle mixing type gas burner, FIG. 17 has shows as premixing type gas burner. At the high combustion 50–70% of theoretical air enters into the mixing tube 1323 after passing through the combustion air damper 1307 to mix with fuel gas, and flows into the combustion inner cylinder 1305 from a flame port 1324; the mixture further mixes to burn with a part of the air in the duct 1311 after passing the cooling air damper 1310 to be a secondary air entering from a secondary air port 1325, the secondary air at this instance is about 50–70% of the theoretical air, the cooling air passing between the combustion inner cylinder 1305 and the combustion outer cylinder 1312 is 2.3 times the theoretical air, and the air volume passing the cooling air damper 1310 is 2.8–3.0 times of the theoretical air.

At the low combustion of 50%, as the combustion air damper slightly closes air about 90–110% of the theoretical air flows into the mixing tube 1323 as the primary air and air of 1.6–1.8 times the theoretical air enters from the cooling air damper 1310, and about 20% of the air, i.e. 35% of the theoretical air is supplied from the secondary air inlet into the combustion inner cylinder 1305 as the secondary air for combustion.

By decreasing the cooling air at the low combustion and controlling the temperature of the combustion outer cylinder, to give the same value as at high combustion, the exhaust gas (at low combustion) is automatically decreased, whereby the heat efficiency of the far infrared ray radiation device (used for the sauna device of this invention) is greatly improved.

Referring to FIGS. 18 to 21, we will discuss the sauna device with the far infrared ray radiation sauna heater which employs the control method of said combustion and air.

This embodiment has as an object to improve the heat efficiency, by employing said control method, it also prevents complication of the combustion mechanism. The invention also permits easy inspection of the components of the combustion system and provides a sauna device (having said for infrared ray radiation device) with has high safety according the present invention.

The far infrared radiation sauna heater using conventional combustion heat provides a supply tube communicating to the combustion tube and the far infrared ray radiating tube which are installed in the sauna chamber. This supply tube passes through the sauna chamber wall from outside of the sauna chamber, and a burner is provided in the supply tube at the sauna chamber end of that tube and the burner has a construction whereby it may be mounted from the sauna chamber side end of the supply tube. The combustion air and the cooling air we suctioned by the exhaust blower. Air flows into the supply tube, from a small hole of said supply tube, which is provided on the end wall of it and at the outside of the sauna chamber.

If the said control method of combustion and air is applied to such device, it is difficult to provide the damper and control motor in the supply tube in a small space area. It also results in complications of the supply tube. It also makes mounting and removing the burner difficult.

Said problem is resolved by a sauna wherein, the device to increase and decrease air by controlling the damper, and the control motor, etc., are located at a suitable position outside the sauna chamber, and two air supply tube communicate between the air controlling device and the combustion and radiating system, the supply tube end on the outside of the sauna chamber and and one of them is to be air supply tube for combustion, another one for air supply tube for cooling the combustion tube.

However, if the above construction is employed, a new problem is raised.

For example, in a conventional device, where the burner is in the supply tube and is detachably connected to the end of the supply tube on the outside of the sauna chamber, where the supply tube is provided in the small through hole on the wall of the sauna chamber, where there is a blower for exhaust, and where a safety device is provided near about, and where furthermore there is and exhaust duct provided between said supply tube end and the blower, the attaching and detaching of the burner should be conducted avoiding these members. Moreover in such a prior device, it is difficult to inspect and repair the burner. If the two air supply tubes are additionally provided to such conventional device, a new problem occurs, namely the attaching and detaching operation of the burner becomes more difficult, and hence maintenance of the device becomes difficult and long working hours are needed for repairs.

The objects of this invention include solving said newly raised problem and improving the before mentioned conventional problems. The improvements achieved by providing a sauna chamber having said far infrared radiation heater, said fuel supply tube, an air supply tube for combustion, (which is mainly used for the combustion and the air supply tube for cooling the burning pipe), which is mainly used to cool the tube in which combustion takes place. Such tubes are individually communicated from outside of the sauna chamber to said combustion tube and to the far infrared ray radiating tube. The burneer is detachably mounted in the combustion tube in the sauna chamber. The controller which automatically increases and decreases the supply of each supply tube is provided outside of the sauna chamber. An air pressure switch, which is operated by the air pressure in the said air supply tube or in the air supply tube for cooling the combustion tube is provided. A safety device is provided which interrupts the fuel supply responding to the operation of the air pressure switch. Each automatic control device is operated such that the of the fuel and air for combustion are increased and decreased at substantially same rate; however in the case of decreasing the fuel supply, decreasing the rate of the air for cooling the combustion tube is set larger than the decreasing rate air for cooling the combustion tube than the decreasing rate of the fuel.

By such construction, attaching and detaching the burner is easily conducted and the heat efficiency of the far infrared ray radiation is sharply improved by decreasing the exhaustion.

Figure 18:
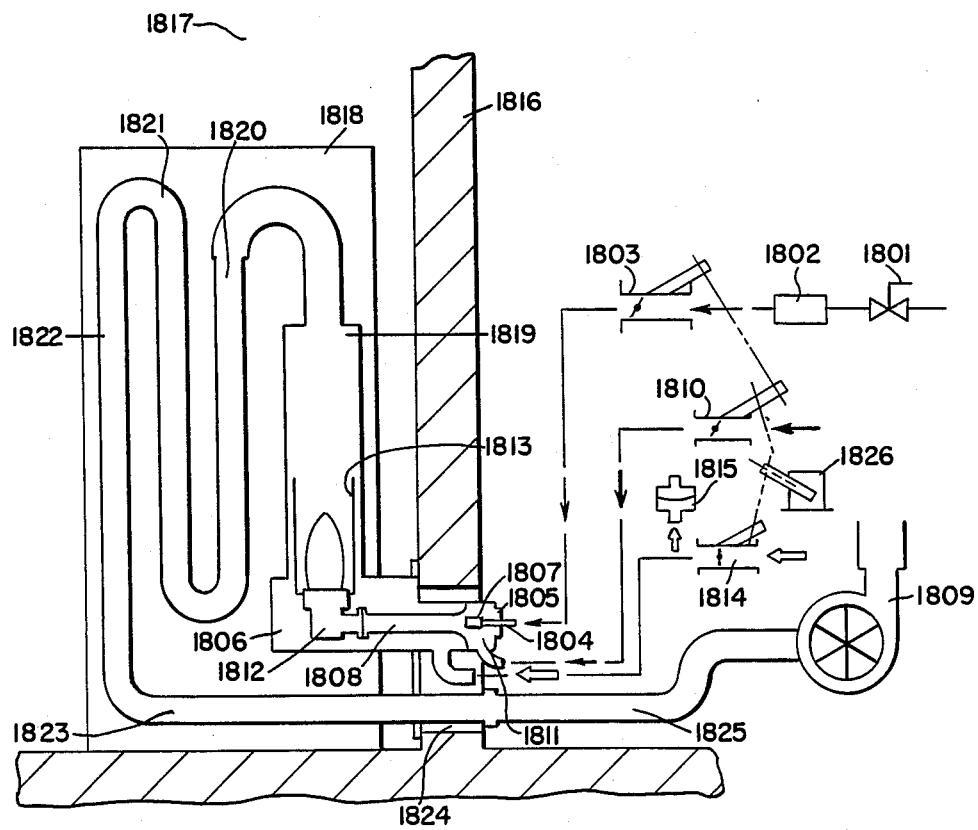
FIG. 18 is a diagram which shows one embodiment of the sauna device of the invention with the far infrared radiation sauna heater employing said control method.
Figure 19:
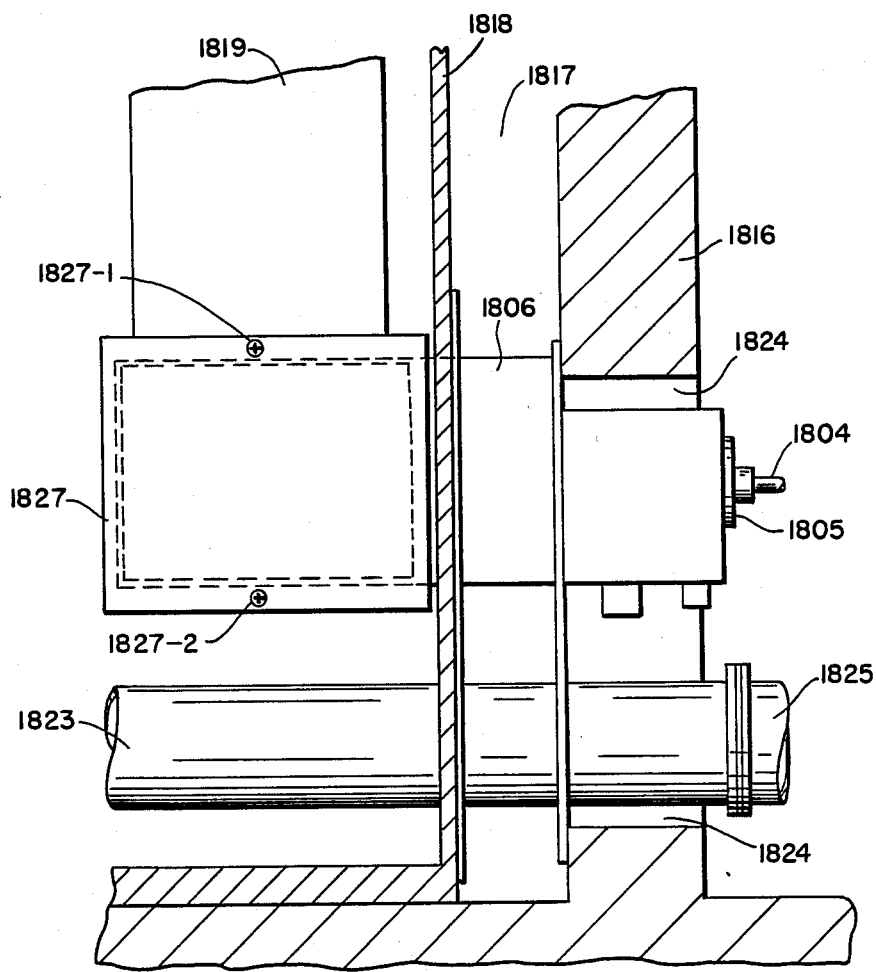
FIG. 19 is a partial enlarged front view of the burner containing part.
Figure 20:
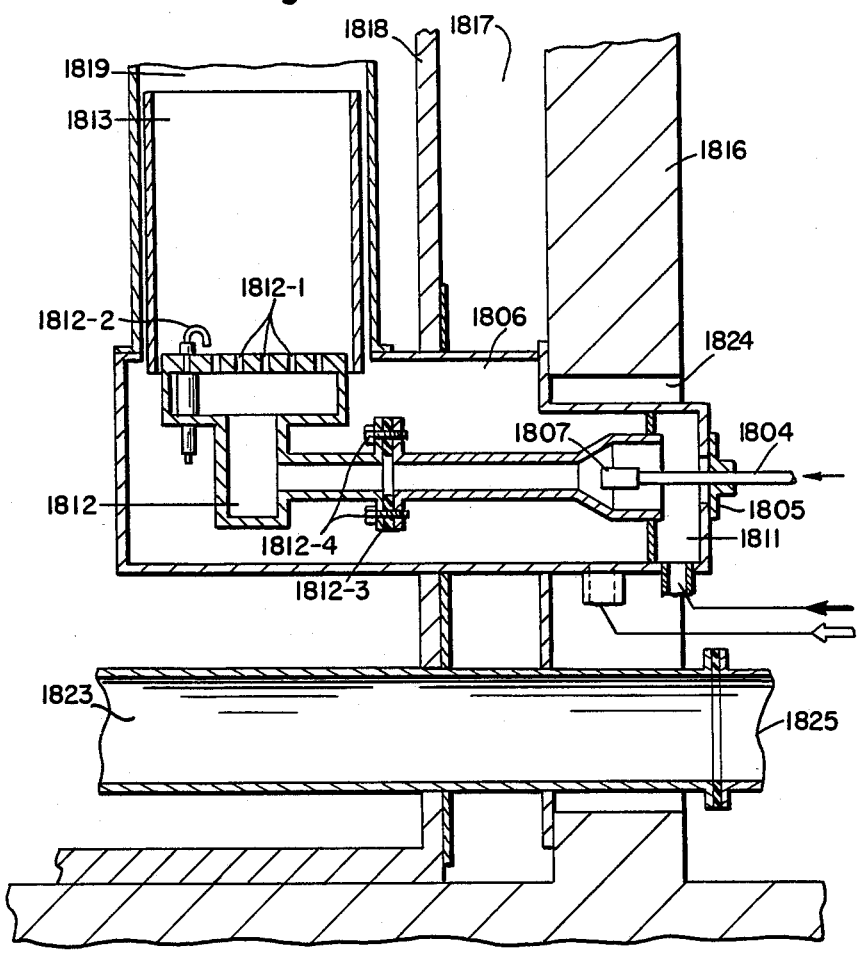
FIG. 20 is a cross section showing inside of FIG. 19.
Figure 21:
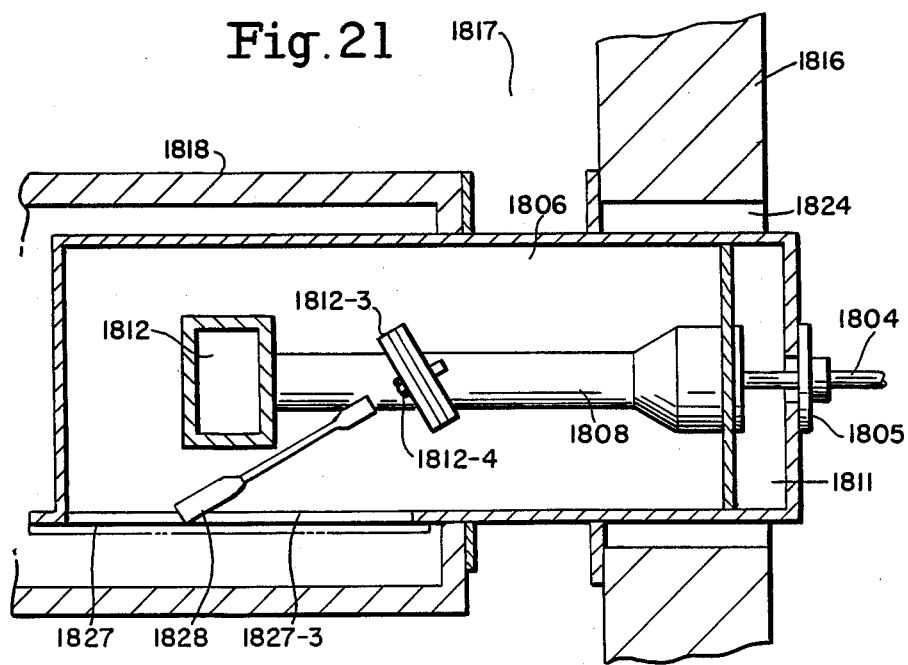
FIG. 21 is a diametral cross section of the blower in FIG. 20.

Now, the further embodiment is explained referring to FIGS. 18–21. FIG. 18 is a diagram showing one embodiment of the sauna device according to the invention having a far infrared ray radiation sauna heater in which said control method is applied, FIG. 19 is a partial enlarged front view showing the burner container, FIG. 20 is a cross section showing the inside of the device shown in FIG. 19, and FIG. 21 is diametric cross section of the blast tube shown in FIG. 20.

In this sauna device, the fuel gas passes from a cock 1801 through a safety device employing an electromagnetic valve etc. 1802, and a gas adjusting valve 1803 and a fuel pipe 1804 provided on a nozzle flange 1805 and flows into a mixing tube 1808 from a gas nozzle 1807 provided at the one end of the mixing tube 1808 partitioned in the blast tube 1806.

Air for combustion is suctioned by a exhaust fan 1809 and enters into a combustion air chamber 1811 in the blast tube 1806 from a combustion damper 1810 along a direction shown by a black fat arrow mark and mixes with the fuel gas in the mixing tube 1808 and this mixed gas flows into the combustion inner tube 1813 from a gas burner 1812 and a flame port 1812-1 and begins burn by igniting by an sparking on plug 1812-2.

Cooling air is taken in from a cooling damper 1814 and pass a branch to the air pressure switch 1815, and enters into the blast tube 1806 from air supply tube for combustion tube cooling which is communicated to the blast tube 1806 and passes the blast tube 1806, and passes between the combustion inner tube 1813 surrounding the ignition port in the combustion tube 1819 of the far infrared ray radiator 1818 and the combustion tube 1819, and rises up cooling outer surface of the combustion inner tube 1813, and gradually joins with the combustion gas cooling inner surface of the combustion tube 1819 and this combustion exhaustion gas passes from upper part of the combustion tube 1819 through the far infrared ray radiator tube, which comprises a first furnace tube 1820, a second furnace tube 1821, a third furnace tube 1822 and a horizontal furnace tube 1823, and passes the exhaustion tube 1825 which passes through a hole 1824 provided on the sauna chamber wall 1816 and toward the outside of sauna chamber, and is suctioned by the exhaust fan 1809, and is exhausted to outside.

The far infrared ray radiation is emitted from the far infrared ray radiation tube surface by the combustion radiation by the above construction thereby the temperature in the sauna chamber 1817 is raised.

On the other hand, FIG. 18 shows a state wherein the control motor 1826 is holding the cooling damper 1814 at a position corresponding to the low combustion rate.

Hence, the gas control valve 1803 and the combustion damper 1810 slightly open (about 30° in the figure) as shown in the figure, but the cooling damper 1814 almost closes.

For the perfect combustion fuel, as the fuel gas and combustion air are increased and decreased at a certain construct rate, the gas control valve 1803 and the combustion damper 1810 open at the same ratio of opening, but as the rate of combustion is low at the low combustion, the temperature of the surface of the combustion inner tube 1813 and the combustion tube 1819 is hardly rises from the temperature thereof at the high combustion rate, and the cooling air for the combustion tube is decreased lesser in comparison with the fuel gas and the combustion air, and for this reason, the cooling air damper 1814 almost closes.

Actually, the opening of the cooling damper 1814 is adjusted by measuring the surface temperature of the combustion inner tube 1813 so that said surface temperature does not exceedingly rises, namely its surface temperature is set about at 400° C. so as to radiate far infrared ray and never exceed 500° C. locally.

When the combustion rate is transferred from the low combustion to the high combustion, the control motor 1826 arm rotates in a counter-clockwise direction from a state shown in the figure by an operation of the thermo-controller operated by the temperature in the sauna chamber, and the cooling damper 1814 is opened to the desired opening rate.

The gas control 1803 and the combustion damper 1810 operate to open for rotary angle almost the same, but the cooling damper 1814 rotates so as to open for a bigger rotary angle; as the opening of the cooling damper 1814 is smaller than the opening of the gas adjuster 1803 and combustion damper 1810 at the low combustion; therefore at the high combustion, the gas adjusting valve 1803 and the combustion damper 1810 and the cooling damper 1814 become to be opened at the same opening in this embodiment.

Summarizing the above, the full supply, the air supply for combustion, and air supply for cooling the combustion tube are controlled ratio of the air supply for combustion/fuel supply becomes generally constant, so that to be monotone decreasing function, and as a result at the low combustion, the exhaustion gas greatly decreases, and hence the heat efficiency is improved.

An air pressure switch 1815 is a safety device which is adapted to confirm that the fuel gas and combustion gas do not leak in the sauna chamber. It keeps the pressure inside of the far infrared ray radiating tube negative. That tube consists of the blast tube 1806, and combustion tube 1819. When the air pressure switch is detecting the negative pressure at a position of the air pressure switch 1815, suction force is raised; because the negative pressure becomes more strong at the lower stream of the far infrared ray radiation tube (comprising the combustion tube 1819 and all the all the furnace tubes in the sauna chamber), and when the air pressure switch 1815 does not detect enough negative pressure necessary for safety, the safety device 1802 automatically closes, by an operation of the air pressure switch 1815, so as to stop combustion by interrupting the fuel supply.

To inspect or repair the gas burner 1812 inside of the blast tube 1806, the worker removes the screws 1827-1, 1827-2 and mounts a cover 1827 for repair as shown in FIG. 19 in the sauna chamber. Then the inspection of the gas burner 1912 and the combustion inner tube 1813 as shown in FIG. 20, become practicable. To remove the gas burner 1812, the worker loosens the mounting screw 1812-4 mounted on a flange 1812-3 of the gas burner 1812 and the mounting portion of the mixing tube 1808 and removes it with gas burner 1812. Then worker can take out the gas burner 1812 from the repair opening 1827-3; slightly lowering the gas burner 1812 in the figure, and removing from the combustion inner tube 1813.

To utilize various kind of fuel gases, there is a need to change the gas nozzle 1807 as required to meet with kind of the gas, for this purpose, removing the nozzle flange 1805 provided at an outside end portion of the blast tube 1806 from outside of the sauna chamber, the worker can take out the gas nozzle 1807 integrally provided with the nozzle flange 1805 to the outside of the sauna chamber.

When the gas burner 1812 is removed as mentioned above, it is required that the mounting screws 1812-4, 1812-4 be removed in the narrow blast tube 1806. This cannot be easily done with handy tools such as a screwdriver, wrench or the like. For this reason, it is advisable to mount a flange 1812-3 (of mounting portion of the gas burner 1812) slanting toward the opening side as shown in FIG. 21. The worker can easily remove the screws 1812-4, 1812-4 inserting a screwdriver from the repair opening 1827-3.

At this point, we summarize advantages of said embodiment devices in comparison with the conventional device, as follows; (1) In the conventional device, the air control damper is provided near the lowermost portion of the combustion heater, i.e. between the horizontal furnace tube 1823 and the exhaustion fan 1809, but in this invention, it is located near the uppermost part thereof.

For this reason, the device of this invention has better safety and it is possible to raise the heat efficiency.

Namely, when the gas is burned in the sauna chamber, far infrared ray radiation is converted to heat, the safety is most requested as the device heats nude persons without any protection. One way to solve this problem is to construct the device wherein the combustion gas does not leak into the sauna chamber by keeping the inner pressure of all the instruments provided in the sauna chamber, namely the far infrared ray radiation tube comprising the combustion tube, and furnace tubes at a negative pressure lower than the atmospheric pressure.

According this measure, the high safety is obtained, as the air in the sauna chamber is exhausted outdoors so that it is not feared that the poisonous combustion gas leaks into the sauna chamber.

However, in the conventional device, as the air is squeezed by the mixed gas damper, the resistance of the damper becames larger and the inside air pressure of furnace tubes, combustion tube, and blast tube approaches atmospheric pressure, and the feature that the combustion as does not leak into the sauna chamber is not present. This reduces the safety.

In the conventional device, at the low combustion for securing safety and for the reason that squeezing the air mix damper near the inlet of the exhaustion fan 1809, the pressure in upstream of the damper approchs atmospheric pressure, and pressure drop of the air pressure switch which is provided near inlet of the exhaustion fan decreases, and the function thereof becomes instable them, the sauna device should be operated opening the damper slightly open, there is a drawback that the exhaustion gas increases for the portion and the heat efficiency is lowered, but in the device of this invention when the blast is squeezed at the lower combustion and the difference pressure of the air pressure switch 1815 increased contrary to the conventional devices, there is no problem of down of the heat efficiency. (2) In the conventional device, as the only one set of the air control damper is provided, it is not available to separately adjust the cooling air and the combustion air, but in the contrast in this device according to this invention as the cooling air damper and combustion air damper are provided, each air can be individually controlled. For this sake, it becomes available that a control method of said combustion and air becomes to be applied to the far infrared ray radiation device for sauna, the heat efficiency at the low combustion of the known conventional device is greatly improved and the fuel gas for sauna chamber heating is reduced for 10% to 20%.

Namely, in the conventional device, the device is operated actually with 5-7 times air of the theoretical air (air rate 5-7).

In contrast, in the device in this invention, (1) as the combustion air damper 1810 and cooling air damper 1814 are separately provided, in the low combustion, the necessary minimum air is supplied, and also (2) as the both damper are provided at the uppermost stream member, the lesser the air is decreased at the low combustion, the lower the pressure falls and safety is increased and operation of the air pressure switch is secured.

Hence, in the low combustion, the combustion air and cooling air are individually controlled.

At the low combustion, the cooling air necessary for keeping the surface temperature of the combustion tube 1819 at 400° C. is hardly to suppose by various factor such as the rate of combustion, etc., but if the air ratio is 3.5 and the temperature of the combustion tube 1819 is about 400° C., it is supposed that the air ratio is about 2.8 at the low combustion reducing the rate of combustion to half.

Supposing that the conventional device operating at air ratio 6 at the low combustion is replaced by the device of this invention, and that at the low combustion, air ratio of the cooling air is 1.5 and total air ratio to be 3, and that the surface temperature of the combustion tube 1819 is able to be kept at 400° C., further supposing that fuel is city gas (13A), 10,000K cal., (higher calorific value) and its theoretical air 10 $Nm^3$, exhaustion temperature 200° C., ambient air temperature 20° C., specific heat of air 0.31K cal/$Nm^3$°C.; the calculate value of the economized heat:

$(6-3) \times 10 \times 0.31 \times (200-20) = 1674$ K cal, in other words, heat of 1674K cal per higher calorific value 1,000K cal. are economized, this means that about 66% in heat efficiency (based on the lower calorific value) improved, to 83% in heat efficiency, the fuel gas of the conventional device is economized for about 20%.

The heat efficiency of the high combustion is actually the same as the conventional one, and 15% economization is achieved in the gas far infrared ray sauna heater in which automatically three position control of high combustion, low combustion and stop is applied.

(3) although in the conventional device, the gas burner 1812 and gas nozzle 1807 can be inserted in and taken out from the end of the blast tube 1806 projected outside of the sauna chamber, in this device of this invention, the gas nozzle 1807 can be inserted in and taken out from the end the blast tube 1806 projected outside of the sauna chamber, the gas burner 1812 from the repair cover 1827 provided on the blast tube 1806 outside of the sauna chamber of 1817. For this design, according the present invention, repair and inspection of the device became easier the service is safely maintained.

Namely, in the conventional device, when the gas burner 1812 is taken out from the blast tube 1806 for repair and inspection, at first an union of the fuel pipe 1804 of copper is demounted, the flange at the end of the blast tube 1806 projected outside of the sauna chamber is together with gas nozzle 1807, finally the gas burner 1812 is taken out integral with the removed mixing tube 1808 to outside the sauna chamber.

The above operation is seen easy, but the through hole 1824 is preferably small from the view point of fire prevention and strength of wall, it is usually made in the allowable minimum size, and as the exhaustion fan 1809 and an exhaustion pipe 1325 are located outside of the through hole 1824, in the sauna chamber, it was difficult to take out gas burner 1812 from the small through hole 1824, avoiding other devices.

In the case wherein the device mechanism conducting the control method of the combustion and air is installed in the conventional device to improve the heat efficiency of low combustion two supply pipes for combustion air and cooling air from the end of the blast tube 1806 to each damper which is installed outside of the sauna chamber, one of which, the air supply tube for combustion, is communicated to the combustion air chamber 1811, there for the said air supply tube for combustion should be replaced when the gas burner 1812 is taken out.

Even in the conventional device, it was difficult to take out the gas burner 1812; as one of the two supply tube has to be removed escaping the two supply tube, it makes the matter still worse.

On the contrary, the device of the invention provides easy take out of the gas burner 1812, removing four screws, namely the two mounting screws 1827-1, 1827-2 of the cover 1827 and the two mounting screws 12-4 of the tube flange 1812-3, operating from inside of the sauna chamber, the gas burner 1812 is easily inspected and repaired.

Furthermore, in the device of this invention, the inspection and repair is more safely and assuredly carried than the conventional device.

Namely, the gas burner 1812 is taken out from the sauna chamber side end of the blast tube 1806 in the conventional device, as it is unpossible to inspect from the end of the blast tube by eyes connection state between the gas burner 1812 and the combustion inner tube 1813 end and damage of the combustion inner tube 1813, on one occasion the fact that the gas burner 1812 is located in slant manner was passed unnoticed, and the combustion inner tube 1813 was damaged and such damage was not found for long time.

On the contrary, in the device of this invention, if the cover for repair 1827 is removed, as the inspection of the connection state of the gas burner 1812 and the combustion inner tube 1813 is carried out maintenance of the device is easily carried out.

In the conventional device, for repair and inspection of the gas burner 1812 the connection such as an union of the fuel tube 4 has to be removed, there is a risk of leakage of the gas caused by mid-binding the mounting screw or wear of packing reconnection, but in the device of this invention, there is no need of the removal of the fuel tube 1804 at repair and inspection of the gas burner 1812, and even if the mixed gas leaks into the blast tube 1806 from the connection of the gas burner 1812 and the mixing tube 1808, the inside of the blast tube 1806 is negative pressure and as there is no fear of leak gas into the sauna chamber, the device is inferior in safety. (4) In the conventional device, the air pressure switch is provided just before the exhaustion fan 1809, to detect pressure of the lowermost part of the combustion mechanism, but in the device of this invention, the pressure of the uppermost part is detected and for this reason, the safety of the device is more improved.

Namely, as the air pressure switch 1815 is provided at the lowermost in the conventional device, as the difference pressure shown by the air pressure switch 1815 rises higher when the inside the furnace tube of upper part from the pressure detecting point of the air pressure switch is chalked by soot, the air pressure switch 1815 applies signal which shows that the device is normal to the safety device, but in the device of this invention, as the air pressure switch 1815 detects the pressure at the uppermost member, it is safe as difference pressure shown by the air pressure switch 1815 decreases. The air switch operates finally, to stop the devices, when the combustion tube 1819 and each tube at downstream from the pressure detecting point or the connection of the tube is pulled out.

It is possible to constitute such that modifying the design of the above embodiment, for example, it is possible to additionally provide a further cooling damper to decrease the air at low combustion, to connect the two sets of cooling dampers in series to decrease the cooling air at the low combustion, and them to use a part of the cooling air at the high combustion as a secondary air for combustion.

As mentioned above, according to the embodiments shown in FIGS. 18 to 21, such sauna device having far infrared ray radiation sauna heater is provided, wherein heat efficiency is greatly improved in comparison to the far infrared ray radiation sauna heater by conventional combustion type, and safety in the sauna chamber is assured, and furthermore, inspection and repair of the burner and the like are easily and quickly conducted.

Thus, the infrared ray radiation sauna device with combustion heat as its heat source according to this invention is compact and safely constituted as mentioned above, and it is suitable for home sauna device. Here after, an embodiment of the sauna device according to the invention which is constructed to be also useable as a drying room in home is explained.

I claim:

1. An infrared radiation sauna device employing burning fuel as a heat source, comprising:
    an enclosure defining a sauna chamber,
    an infrared radiating tube in said sauna chamber, said tube having an outer wall for radiating heat and an inner wall, said tube having a downstream end,
    means for heating the inner wall to thereby raise the temperature of the outer wall so that heat is radiated from said outer wall, said means including apparatus for providing and burning fuel, said apparatus including a fuel pipe, for delivering the fuel to be burned,
    a seat in said sauna chamber positioned so that a person on said seat will be spaced from said tube and located in the path of radiation from said tube,
    said enclosure defining a space under said seat, at least a part of said apparatus being located in said space,
    an exhaust pipe connected to and extending from said downstream end, and passing through said space under said seat, for exhausting burned gases outside of said enclosure,
    said seat being removable to enable access to be gained to said space for repair of the contents thereof.

2. An infrared radiation sauna device as defined in claim 1 including a blower, in said space, for exhausting the exhaust gases in said exhaust pipe.

3. An infrared radiation sauna device as defined in claim 1, comprising:
    said fuel being gas,
    said fuel pipe having a valve in the pipe for controlling the flow of gas to be burned, said valve being located in said space under said seat.

4. An infrared radiation sauna device as defined in claim 3 comprising:
    a blower in said space for exhausting the gases in said exhaust pipe.

5. An infrared radiation sauna device as claimed in claim 4 in which said seat includes insulating material to isolate anyone sitting on said seat from any heat in said space.

6. An infrared radiation sauna device as defined in claim 1, comprising:
    a box extending around said space, said box having an upper horizontal wall constituting said seat,
    said box having at least one side wall,
    at least one of said walls being easily removable to permit the contents of the box to be repaired.

7. An infrared sauna device as defined in claim 6, comprising:
    a blower in said box and positioned in said exhaust pipe for exhausting burned gases, and
    valve means in said box for controlling the flow of fuel in said fuel pipe.

* * * * *